US00PP36784P2

(12) United States Plant Patent
Smith

(10) Patent No.: US PP36,784 P2
(45) Date of Patent: Jul. 1, 2025

(54) STRAWBERRY PLANT NAMED 'LADY GRACE'

(50) Latin Name: ***Fragaria* x *ananassa* (Duch.)**
Varietal Denomination: Lady Grace

(71) Applicant: S&A Soft Fruits Ltd., Marden (GB)

(72) Inventor: Dan Smith, Herefordshire (GB)

(73) Assignee: S&A Soft Fruits Ltd., Marden (GB)

( * ) Notice: Subject to any disclaimer, the term of this patent is extended or adjusted under 35 U.S.C. 154(b) by 0 days.

(21) Appl. No.: 18/770,593

(22) Filed: Jul. 11, 2024

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./209

CPC ..... A01H 5/08; A01H 5/00; A01H 6/7409; A01H 6/74
See application file for complete search history.

(56) References Cited

U.S. PATENT DOCUMENTS

PP32,466 P2 * 11/2020 Geoghegan ..... A01H 5/08 Plt./209

OTHER PUBLICATIONS

UPOV PLUTO Plant Variety Database Oct. 28, 2024, retrieved on Oct. 29, 2024 at https://pluto.upov.int/result, one page. (Year: 2024).*

* cited by examiner

*Primary Examiner* — June Hwu
(74) *Attorney, Agent, or Firm* — The Webb Law Firm

(57) ABSTRACT

A new and distinct strawberry plant is provided that exhibits a spreading growth habit with juicy and glossy fruit displayed on long peduncles.

4 Drawing Sheets

Botanical classification: *Fragaria* x *ananassa* (Duch.).
Varietal denomination: 'Lady Grace'.

BACKGROUND OF THE INVENTION

The present invention comprises a new and distinct variety of strawberry plant botanically classified as *Fragaria* x *ananassa* (Duch.) and known by the varietal name 'Lady Grace'. The new variety was originally referred to as RD479-001-2015. The new variety is the result of a cross between strawberry seedling referred to as SA122 (female parent, unpatented) and strawberry seedling referred to as SA11 (male parent, unpatented). The resultant cross produced 'Lady Grace' in July of 2016 in Herefordshire, United Kingdom. The purpose of the breeding program was to develop novel everbearing and day neutral strawberry varieties. Subsequently, the new variety was asexually reproduced via stolons in Herefordshire, United Kingdom in August of 2016. The new variety has been trial and field tested and has been found to retain its distinctive characteristics and remain true to type through successive asexual propagations. The new variety has not been evaluated under all possible environmental conditions. The phenotype may vary with variations in environment without a change in the genotype of the plant.

The new variety is similar to its female parent in having vigorous growth with long petioles and peduncles. However, 'Lady Grace' differs from its female parent in exhibiting a paler berry skin color, but with a glossier finish. The new variety is similar to its male parent in having consistently sweet berries with a strong skin. However, 'Lady Grace' differs from its male parent in having larger berries with a softer fruit flesh.

When compared to strawberry variety named 'Lady Emma' (U.S. Plant Pat. No. 32,466), 'Lady Emma' has a more compact growth habit, as the plants of 'Lady Grace' are generally 30-40% taller than 'Lady Emma'. The flowers of 'Lady Grace' are displayed well above the canopy on long peduncles and petioles, while those of 'Lady Emma' are generally displayed on or slightly below the canopy. The sepals of 'Lady Emma' terminate in an acute point, whereas the sepals of 'Lady Grace' alternate between acute (sepals) and obtuse (episepals) termination.

The following characteristics also distinguish the new variety from other strawberry varieties known to the breeder:

- Highly productive variety, typically 1.8 kg per plant, that produces juicy berries with a sweet and lightly floral aroma;
- Alternating shape of sepal termination point;
- Glossy berries with a slightly inverted calyx that are displayed on long peduncles;
- Pistil will often remain attached from fertilization through to full fruit and achene maturation;
- The petals will occasionally develop a localized light pink/purple hue after flower pollination; and
- Tall plant height, with the flowers displayed well above the canopy on long peduncles.

DESCRIPTION OF THE DRAWINGS

The accompanying photographic drawings illustrate the new variety at approximately 10 months of age, with the color being as nearly true as is possible with color illustrations of this type.

DESCRIPTION OF THE PLANT

Figure 1:
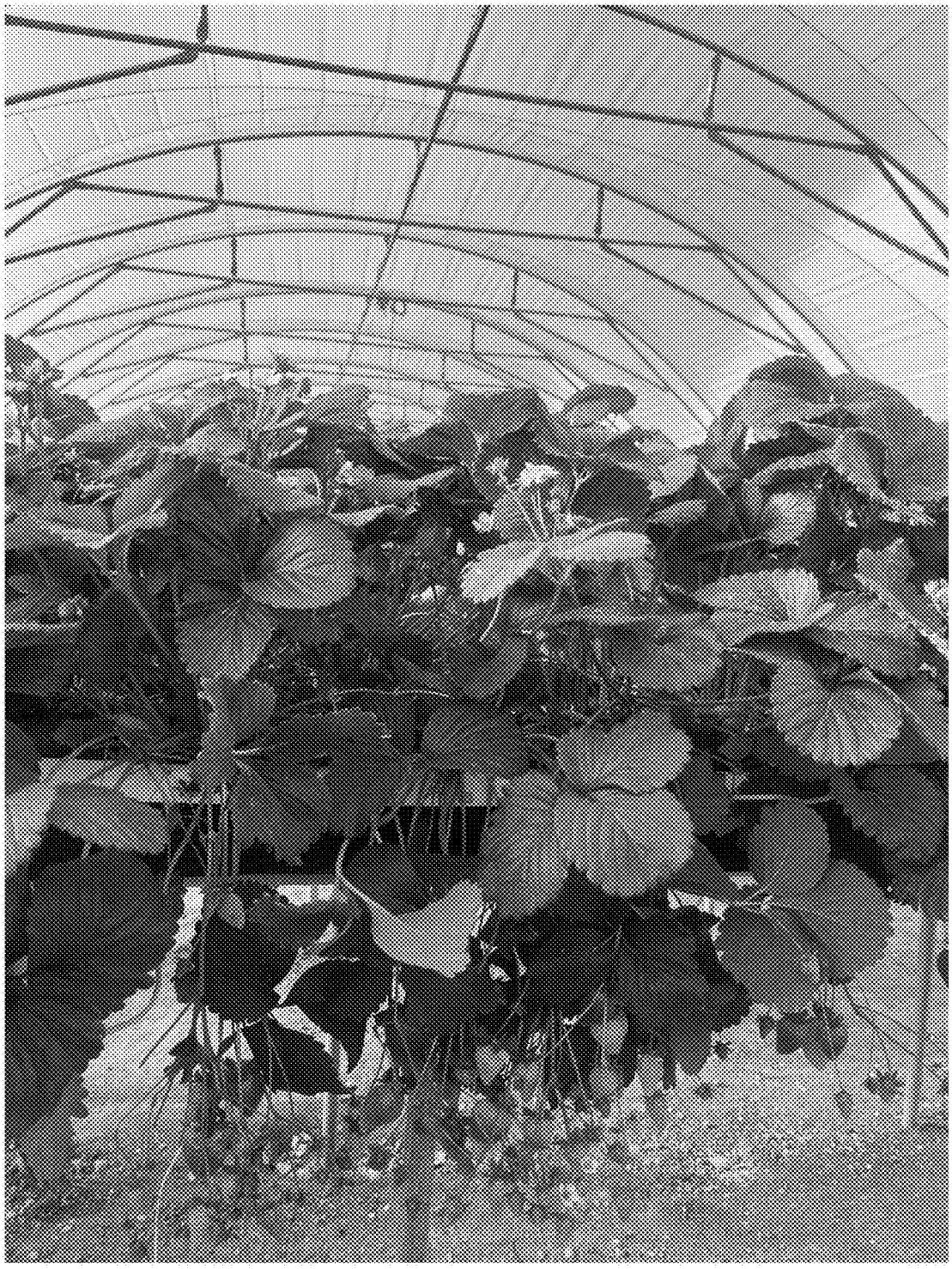
FIG. 1 is a photograph of multiple plants of the new variety.
Figure 2:
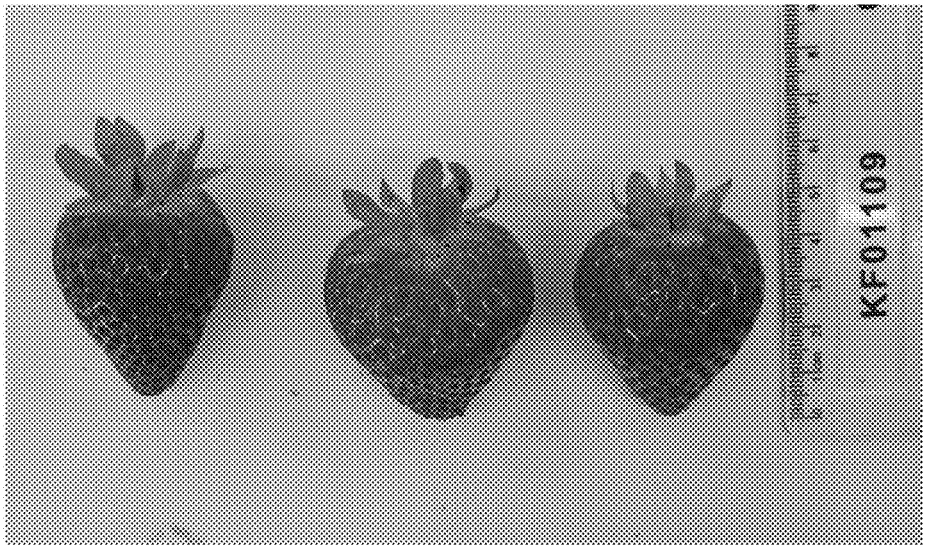
FIG. 2 is a photograph of whole fruits of the new variety.
Figure 3:
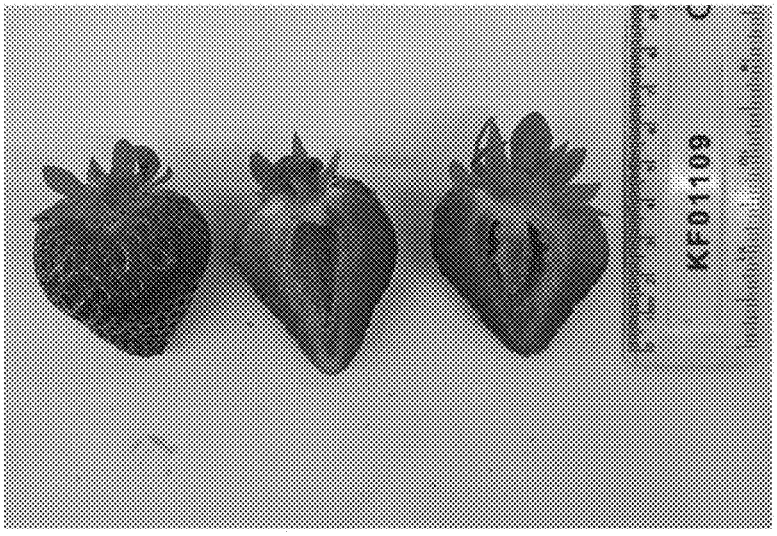
FIG. 3 is a photograph of fruits of the new variety.
Figure 4:
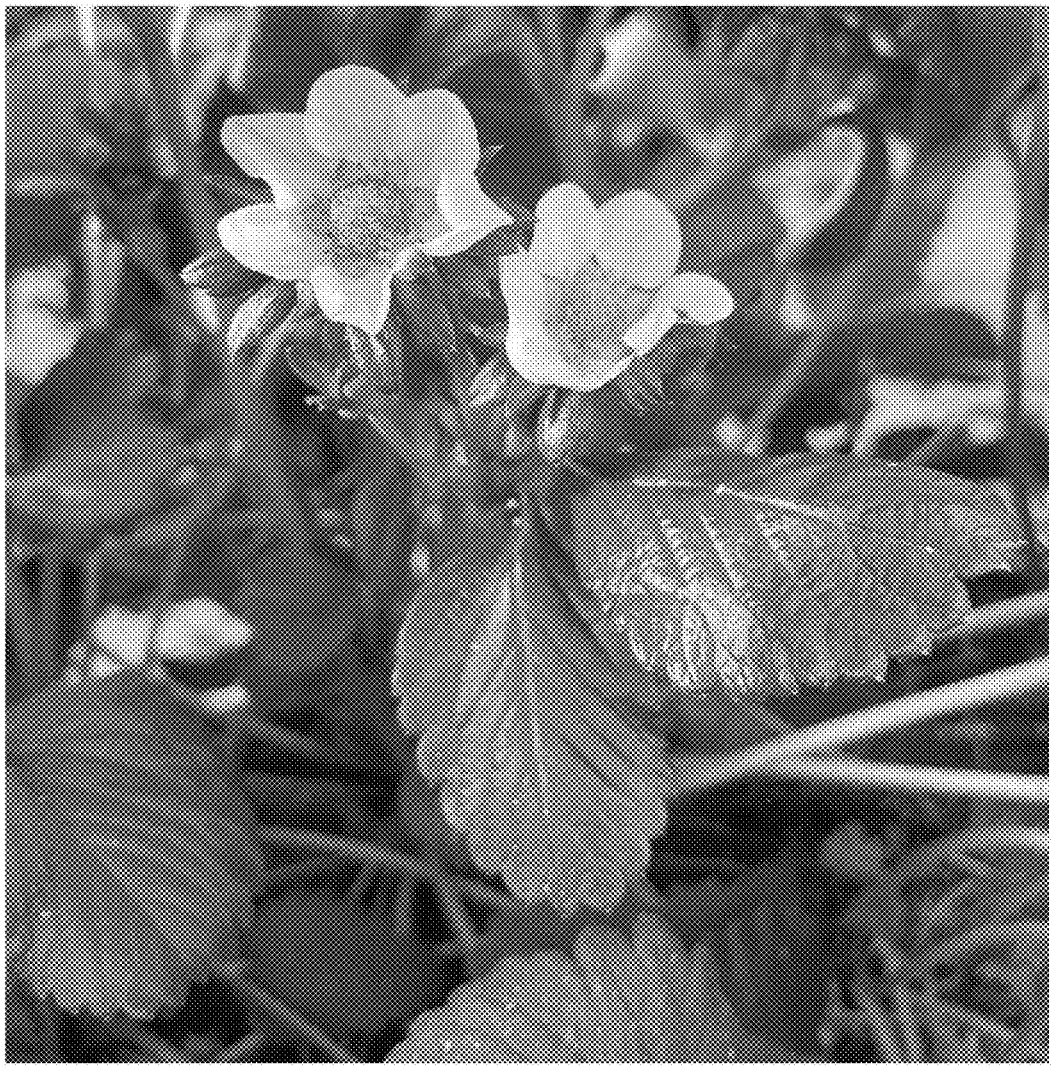
FIG. 4 is a photograph of flowers of the new variety.

The following detailed description sets forth the characteristics of the new cultivar. The new variety was grown under polytunnel protection in 2 liter containers in Herefordshire, United Kingdom with an average day temperature of 18° C. and an average night temperature of 12° C. The new variety was approximately 12 months of age when described. Color references are primarily to the Sixth Edition (2015) of The R.H.S. Colour Chart of The Royal Horticultural Society of London and were identified under natural light.

PLANT

Time to initiate roots: 48 hours at an average temperature of 20° C.

Time to produce a rooted plant: 30 days at an average temperature of 20° C.

Rooting habit: Vigorous.

Plant form: Spreading.

Height (from soil to top of plant): Average 24.5 cm, range 22-30 cm.

Plant diameter: Approximately 67 cm.

Vigor: Moderate to high.

Disease/pest resistance: Resistant to crown rot.

Weather tolerance: Plants perform best in a protected environment and tolerate temperatures from −3° C. to 38° C.

Foliage:

- *Arrangement*.—Basal rosette; upwardly forming.
- *Average number of leaves per crown*.—10-15.
- *Whole leaf length*.—Average 9.1 cm, range 6.5-12 cm.
- *Whole leaf width*.—Average 16.5 cm, range 12-23 cm.
- *Rugosity*.—Weak.
- *Glossiness*.—Medium.
- *Petiole*.—Length: Average 17.5 cm, range 12-25 cm. Diameter: Average 5.1 mm, range 3-7 mm. Color: RHS 145A to 145B. Texture: Pubescence outwardly facing.
- *Stipule*.—Average number per leaf: 2. Length: Average 3.4 cm, range 3-4 cm. Width: Average 8 mm, range 5-10 mm. Color: RHS 144D to 144C.
- *Color*.—Young leaflets: Upper surface: RHS 143B. Lower surface: RHS 144B. Mature leaflets: Upper surface: RHS 137B. Lower surface: RHS 146D.
- *Lateral leaflets*.—Length: 5-13 cm. Width: 4-11 cm. Shape of leaf (generally): Typically orbicular, basally asymmetrical, cross-sectionally concave at the base changing to convex at the apex. Shape of apex: Obtuse. Shape of base: Oblique. Texture (both surfaces): Lightly pubescent. Aspect: Upright. Margin type: Crenate.
- *Terminal leaflets*.—Length: Average 7.7 cm, range 4.5-10 cm. Width: Average 7.7 cm, range 4.5-10 cm. Shape of leaf (generally): Cross-sectionally concave. Shape of apex: Obtuse. Shape of base: Acute. Texture (both surfaces): Lightly pubescent. Aspect: Upright. Margin type: Crenate.
- *Veins*.—Venation pattern: Pinnate. Color: Upper surface: RHS N144D. Lower surface: RHS 145B.

Fruit:

- *Harvest season*.—From April-December in Herefordshire, United Kingdom.
- *Number of fruit per fruiting lateral*.—6.
- *Calyx attachment*.—Level with fruit.
- *Width of band without achenes*.—Narrow.
- *Surface color*.—Immature: RHS 144D. Maturing: RHS 145C. Fully mature: From RHS 44C to 44B. Evenness of color: Uneven.
- *Aroma*.—Sweet and lightly floral.
- *Brix reading*.—7.5 Average.
- *Acidity*.—0.49 Average.
- *Length*.—Average 5.5 cm, range 5-7 cm.
- *Width*.—Average 31.8 mm, range 30-41 mm.
- *Length/width ratio*.—Longer than wide.
- *Overall shape*.—Conical.
- *Glossiness*.—Strong.
- *Weight*.—Average of 20.5 grams across a growing season.
- *Achene position*.—At surface level.
- *Achene color*.—From RHS 151A to 151B.
- *Average number of achenes per berry*.—300.
- *Flesh firmness*.—Medium.
- *Flesh color*.—RHS 33A to 33B.
- *Fruit core size*.—Small.
- *Fruit core color*.—RHS 34B to 34C.
- *Fruiting truss length*.—Average 33 cm, range 32-41 cm.
- *Fruiting truss diameter*.—Average 5.5 mm, range 4-6 mm.
- *Fruiting truss color*.—RHS 145A.
- *Shipping quality*.—Able to be shipped via refrigerated transport (4° C.).
- *Storage life*.—Up to 4 days post-harvest.
- *Market use*.—Primarily fresh market.

Reproductive organs:

- *Stamens*.—Number per flower: Average 21.2, range 15-28. Length: Average 4.14 mm, range 3-6 mm. Width: 1 mm.
- *Anthers*.—Apex shape: Rounded. Base shape: Cordate. Length: 2-3 mm. Width: 1 mm. Color: Edge: RHS 12A. Center: RHS 7A.
- *Stigma*.—Texture: Lightly papillose. Shape: Rounded to acute. Color: RHS 3A to 3B.
- *Style*.—Length: 1.5 mm. Color: RHS 4A.
- *Ovary*.—Texture: Pubescence present. Length: 1 mm. Color: With seed: RHS 140B. Without seed: RHS 144C.
- *Stolon*.—Length: Mother plant to first stolon-plant: Approximately 63 cm. Mother plant to second stolon-plant: Approximately 96 cm. Diameter: Approximately 23 mm. Color: RHS 145B.

Flowers:

- *Natural flowering season*.—From February-December in Herefordshire, United Kingdom.
- *Number of flowers per plant*.—80-120.
- *Fragrance*.—None present.
- *Longevity*.—4-7 days.
- *Flower description*.—Rotate flowers arranged singly at lateral apices that are cupped upwards and with slight overlap of petals.
- *Flower height*.—Average 10.3 mm, range 10-15 mm.
- *Flower diameter*.—Average 31.2 mm, range 28-33 mm.

*Petals*.—Number per flower: 6. Shape: Globose to obovate. Length: Average 15 mm, range 14-17 mm. Width: Average 16 mm, range 15-18 mm. Apex: Rounded. Base: Acute point. Margin: Entire. Texture (both surfaces): Smooth, with no pubescence present. Color: Mature petal: Upper surface: RHS 155C. Lower surface: RHS 155D. Young petal: Upper surface: RHS 155C. Lower surface: RHS 155C. Occasionally following pollination: RHS 66B-66C.

*Sepals*.—Number per flower: Average of 10 (does not include episepals). Attitude: Upwards. Length: Average of 10 mm. Width: Average of 6 mm. Shape: Lanceolate with typically a single apex; can be multi-pointed on primary flowers. Apex: Acute. Margin: Entire. Texture: Pubescence present on both upper and lower surfaces. Color: Mature sepal: Upper surface: RHS 138A. Lower surface: RHS 138B. Young sepal: Upper surface: RHS 141B. Lower surface: RHS 141C.

*Episepals*.—Length: Average of 7 mm. Width: Average of 4 mm. Apex: Acute. Color: Upper Surface: RHS 141B. Lower Surface: RHS 141C.

*Buds*.—Length: Average 8 mm, range 7-10 mm. Diameter: Average 8 mm, range 5-10 mm. Shape: Ovoid. Color: RHS 143C to 143B.

I claim:

1. A new and distinct variety of strawberry plant named 'Lady Grace', as is herein illustrated and described.

* * * * *